United States Patent

Jackson et al.

Patent Number: 4,532,322
Date of Patent: Jul. 30, 1985

[54] PREPARATION OF THIAZINE DERIVATIVES

[75] Inventors: Arthur Jackson, Washington; Graham Heyes, Durham, both of England

[73] Assignee: Fine Organics Limited, Middlesbrough, England

[21] Appl. No.: 613,104

[22] Filed: May 23, 1984

[30] Foreign Application Priority Data

May 23, 1983 [GB] United Kingdom ............... 8314245

[51] Int. Cl.³ .......................................... C07D 279/04
[52] U.S. Cl. ................................................... 544/54
[58] Field of Search ......................................... 544/54

[56] References Cited

U.S. PATENT DOCUMENTS 3,993,648 11/1976 Powell ................................. 544/54
4,013,766 3/1977 Roman ................................ 544/54

*Primary Examiner*—John M. Ford
*Attorney, Agent, or Firm*—Bert J. Lewen

[57] ABSTRACT

A method for the preparation of a thiazine derivative of the formula

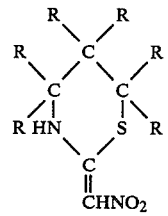

where each R is independently selected from hydrogen or a lower alkyl having 1 to 4 carbon atoms, the method comprising reacting together a sulphur donor which is selected from sulfur, ammonium or alkali metal sulfides, ammonium or alkali metal hydrosulfides, or hydrogen sulfide, 1,1-bis(methylthio)-2-nitroethene and a compound of the formula $H_2NCR_2CR_2CR_2OSO_3H$ where each R is as defined above.

A preferred method is for the preparation of tetra-2-(nitromethylene)-2H-1,3-thiazine which possesses broad spectrum insecticidal activity, and is also useful as an intermediate in the synthesis of other insecticides.

7 Claims, No Drawings

PREPARATION OF THIAZINE DERIVATIVES

INTRODUCTION

This invention relates to methods of preparing thiazine derivatives which have insecticidal activity.

Tetrahydro-2-(nitromethylene)-2H-1,3-thiazine (I) possesses broad spectrum insecticidal activity, being particularly active against lepidopterous larvae on plants. It is also useful as an intermediate in the synthesis of more stable but equally active insecticides e.g., the oxime of 5,6-dihydro-4H-1,3-thiazine-2-carboxaldehyde (II).

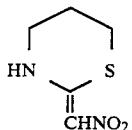
I

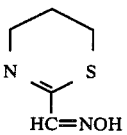
II

The two known synthetic methods for preparing compound I are outlined below:

Route A

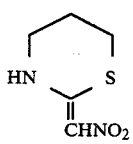

Route B

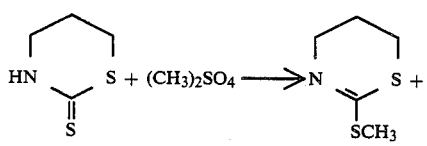

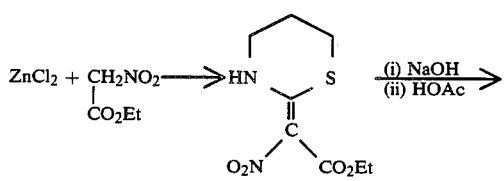

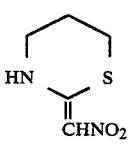

Route A suffers from the disadvantage that the starting material 3-aminopropane thiol hydrochloride is expensive and the yield by this route is only moderate.

Although the starting material for Route B, tetrahydro-1,3-thiazine-2-thione, is relatively inexpensive the ethyl nitroacetate required in the second stage of the synthesis is not available in commercial quantities and this rules out this procedure for manufacturing on an industrial scale.

STATEMENT OF INVENTION

According to the present invention there is provided a method for the preparation of a thiazine derivative of the formula

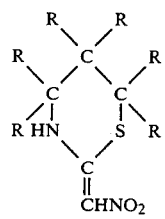

where each R is hydrogen or an appropriate aromatic or aliphatic substituent, the method comprising reacting together a sulphur donor, 1,1-bis(methylthio)-2-nitroethene and a compound of the formula $$H_2NCR_2CR_2CR_2OSO_3H$$

where each R is as defined above.

Preferably, each R is independently hydrogen or lower ($C_1$–$C_4$) alkyl and more preferably each R is hydrogen.

The sulphur donor may be any suitable source of sulphur, for example, sulphur itself, a sulphide, a hydrosulphide or hydrogen sulphide. Preferably, the sulphur donor is an ammonium or alkali metal sulphide or hydrosulphide, for instance, the alkali metal sulphide sodium sulphide.

PREFERRED METHOD

A preferred method in accordance with the present invention may be represented as follows (taking the case, by way of example, where each group R is hydrogen):

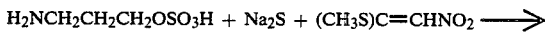

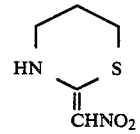

The starting aminopropylsulphate is easily prepared from 3-amino-propanol and sulphuric acid. The preferred reaction referred to above proceeds at room temperature and this would appear to rule out a reaction mechanism involving the formation of the aminopropanethiol since it is known that the formation of the thiol only occurs at an appreciable rate at temperatures greater than 80° C. It may be that the reaction mechanism involves an initial attack by the sulphide anion on the nitroethene in a Michael type addition. The resultant thiol anion may then displace the sulphate ion in the aminopropyl sulphate. Ring closure with the elimination of two molecules of methyl mercaptan then occurs to give the product.

This mechanism is also supported by the fact that an excess of sodium sulphide increases the yield obtained by the reaction. Using molar quantities of the reactants results in a yield of the order of 10% whereas a 50-100% excess of sodium sulphide increases the yield to 40-50%.

It is also advantageous to use an excess of up to 50% of the aminopropyl sulphate.

Because of the insolubility of the bis(methylthio) nitroethane in water it can be advantageous to use a cosolvent. However, the reaction may be carried out in the presence or absence of a cosolvent. Preferred cosolvents are ethanol, ethylene dichloride, benzene and toluene. More preferably the reaction is conducted in the absence of a cosolvent or with ethylene dichloride, benzene or toluene, especially benzene, as the cosolvent.

The molar ratios of the reactants are not critical but, so as fully to utilise the more expensive bis-S-methyl compound, it is preferred to use an excess (5-15%) of sodium sulphide and amino propyl sulphate.

The concentration of the reactants in the solvent (or cosolvent system) is not critical. However, sodium sulphate tends to come out of the solution at the end of the reaction and it is desirable to keep the overall concentrations sufficiently low to avoid this.

Preferably the reaction is conducted at a temperature in the range from 0°–120° C. although products formed at the higher temperatures are relatively more contaminated and more difficult to purify. To obtain a relatively fast reaction time, a high yield and an acceptably low impurity level, a preferred reaction temperature is in the range 60°–80° C.

Examples of methods in accordance with the present invention will now be described.

EXAMPLE I

To a stirred flask fitted with a condenser attached to a caustic hypochlorite scrubbing unit there was charged water (200 ml), ethanol (200 ml), 1,1 bis(methylthio)-2-nitroethene (82.5 g), aminopropylsulphate (120 g) and sodium sulphide (100 g—60% active). The mixture was stirred at room temperature for 12 hours.

The ethanol as distilled out under reduced pressure. Sufficient water was added to dissolve the inorganic salt aand acetic acid was added to cause the pH of the solution to be 5.5. The reaction product was then extracted with chloroform (3×100 ml). The chloroform was distilled out and the product recrystallised from isopropanol to given 32 g of tetrahydro-2-(nitromethylene)-2H-1,3-thiazine having a melting point of 73°–76° C.

EXAMPLE II

To a stirred flask fitted with a conenser attached to a caustic hypochlorite scrubber were charged water (200 ml), benzene (200 ml), 1,1, bis(methylthio)-2-nitroethene. (82.5 g), aminopropyl sulphate (120 g) and sodium sulphide (100 g—60% active). The mixture was then heated to reflux (about 78° C.) with the evolution of methyl mercaptan.

When the evolution was complete (about 1 hour) the reaction solution was cooled, the aqueous layer separated off and the pH adjusted to 5.5 with acetic acid.

The aqueous layer was then extracted with methylene chloride (3×100 ml). The methylene chloride was distilled out and the product recrystallised from isopropanol to give 54.5 g of tetrahydro-2-(nitromethylene)-2H-1,3,-thiazine having a melting point of 73°–76° C.

We claim:

1. A method for the preparation of a thiazine derivative of the formula

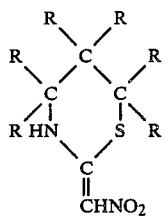

where each R is independently selected from hydrogen or a lower alkyl having 1 to 4 carbon atoms, the method comprising reacting together a sulphur donor which is selected from sulfur, ammonium or alkali metal sulfides, ammonium or alkali metal hydrosulfides, or hydrogen sulfide, 1,1-bis(methylthio)-2-nitroethene and a compound of the formula

where each R is as defined above.

2. A method according to claim 1 wherein each R is hydrogen.

3. A method according to claim 1 wherein the sulphur donor is an ammonium or alkali metal sulphide or hydrosulphide.

4. A method according to claim 1 wherein the sulphur donor and the compound of the formula H$_2$NCR$_2$CR$_2$CR$_2$OSO$_3$H are used in an excess of 5-15% based on the moles of 1,1-bis(methylthio)-2-nitroethene used.

5. A method according to claim 1 wherein the reaction is conducted at a temperature of from 60°–80° C.

6. A method according to claim 1 wherein the reaction is conducted in the absence of a cosolvent or using as cosolvent a solvent selected from the group consisting of ethylene dichloride, benzene and toluene.

7. A method for the preparation of a thiazine derivative of the formula

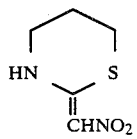

comprising reacting together an alkali metal sulphide, 1,1-bis(methylthio)-2-nitroethene and a compound of the formula

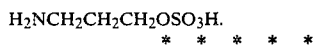

* * * * *